United States Patent
Honczarenko et al.

(10) Patent No.: US 11,466,091 B2
(45) Date of Patent: Oct. 11, 2022

(54) METHODS OF TREATING AUTOIMMUNE DISEASE USING A DOMAIN ANTIBODY DIRECTED AGAINST CD40L

(71) Applicant: BRISTOL-MYERS SQUIBB COMPANY, Princeton, NJ (US)

(72) Inventors: Marek Honczarenko, Princeton, NJ (US); Vaishali Shah, Pennington, NJ (US); Lixin Lang, Princeton, NJ (US); Urvi Aras, Kendall Park, NJ (US); Diane Shevell, Westfield, NJ (US); Christine Kratt, Fort Collins, CO (US); Karen Price, Sauquoit, NY (US); Suzanne Suchard, Portland, OR (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 133 days.

(21) Appl. No.: 16/795,823

(22) Filed: Feb. 20, 2020

(65) Prior Publication Data
US 2020/0216552 A1    Jul. 9, 2020

Related U.S. Application Data

(63) Continuation of application No. 15/510,507, filed as application No. PCT/US2015/049338 on Sep. 10, 2015, now abandoned.

(60) Provisional application No. 62/048,459, filed on Sep. 10, 2014.

(51) Int. Cl.
| | |
|---|---|
| C07K 16/28 | (2006.01) |
| A61K 39/395 | (2006.01) |
| A61K 45/06 | (2006.01) |
| A61K 39/00 | (2006.01) |

(52) U.S. Cl.
CPC ...... *C07K 16/2875* (2013.01); *A61K 39/3955* (2013.01); *A61K 45/06* (2013.01); *A61K 2039/505* (2013.01); *A61K 2039/54* (2013.01); *A61K 2039/545* (2013.01); *C07K 2317/52* (2013.01); *C07K 2317/56* (2013.01); *C07K 2317/565* (2013.01); *C07K 2317/569* (2013.01); *C07K 2317/76* (2013.01); *C07K 2317/94* (2013.01); *C07K 2319/00* (2013.01)

(58) Field of Classification Search
None
See application file for complete search history.

(56) References Cited

U.S. PATENT DOCUMENTS

2013/0095109 A1    4/2013    Nadler et al.

FOREIGN PATENT DOCUMENTS

| WO | WO2013056068 A1 | 4/2013 |
| WO | WO2016040571 A1 | 3/2016 |

OTHER PUBLICATIONS

Piche-Nicholas et al., MAbs. 2018; 10: 81-94. doi: 10.1080/19420862. 2017.1389355 (Year: 2018).*
Wakwe et al., Transplantation, (Jul. 15, 2014) vol. 98, Supp. Suppl. 1, pp. 680-681. Abstract No. C3048. Presented at Meeting Info: 2014 World Transplantation Congress, WTC 2014. San Francisco, CA, United States (Year: 2014).*
Chen et al., Cellular & Molecular Immunology; 2006; 3: 163-169.
International Preliminary Report for PCT/US2015/049338 dated Mar. 14, 2017.
Ke et al., Journal of Neuroimmunology; 2005; 164; 85-92.
Patel, Vivek L., et al., The effect of anti-CD40 ligand in immune thrombocytopenic purpura, British Journal of Haematology, vol. 141, No. 4 (May 1, 2008), pp. 545-548.
Report on Letolizumab: Study IM140-103 MAD Study, Bristol-Myers Squibb internal document, Apr. 1, 2019.
Rodeghiero et al., Blood; 2009; 113; 2386-2393; 2009.
Shih, Andrew, et al., "Novel treatments for immune thrombocytopenia," Presse Medicale, vol. 43, No. 4 (Apr. 1, 2014), pp. e87-e95.
Xie, J.H. et al, "Engineering of a Novel Anti-CD40L Domain Antibody for Treatment of Autoimmune Diseases," The Journal of Immunology, vol. 192, No. 9, (Mar. 26, 2014), pp. 4083-4092.

* cited by examiner

*Primary Examiner* — Christina M Borgeest

(57) ABSTRACT

Methods of treating autoimmune diseases, such as primary immune thrombocytopenia (ITP), solid organ transplant rejection, graft-related disease, pemphigus vulgaris, systemic sclerosis, and myasthenia gravis using antibody polypeptides that specifically bind human CD40L are provided. The antibody polypeptides do not activate platelets. The methods may comprise at least one administration cycle comprising one dose of the antibody polypeptide. The dose may be administered intravenously at a dose from about 75 mg to about 1500 mg. The method normalizes platelet counts in the human patient.

16 Claims, 4 Drawing Sheets

Specification includes a Sequence Listing.

FIG. 1B

EVQLLESGGGLVQPGGSLRLSCAASGFTFNWELMGWARQAPGKGLEWVSGIEGPGDVTYYADSVKGRFTISRDNSKNTLYLQMNSLRAEDTAVYY
CVKVGKDAKSDYRGQGTLVTVSSASTEPKSSDKTHTSPPSPAPELLGGSSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHNHYTQKSLSLSPGK
(MW=77,984 daltons)

dAb
Linker
Modified IgG1 Fc from Abatacept (Cys→Ser; Pro→Ser)

METHODS OF TREATING AUTOIMMUNE DISEASE USING A DOMAIN ANTIBODY DIRECTED AGAINST CD40L

CROSS REFERENCE TO RELATED APPLICATIONS

This application is a continuation application of U.S. Pat. Ser. No. 15/510,507 filed Mar. 10, 2017, which is a 35 U.S.C. § 371 National Stage Patent application of International Application PCT/US2015/049338, filed Sep. 10, 2015, which claims priority to U.S. Provisional Application Ser. No. 62/048,459, filed Sep. 10, 2014; the entire contents of which are incorporated herein by reference.

TECHNICAL FIELD

Methods of treating autoimmune diseases, such as primary immune thrombocytopenia, solid organ transplant rejection, graft-related disease, pemphigus vulgaris, systemic sclerosis, and myasthenia gravis using antibody polypeptides that specifically bind human CD40L are provided.

BACKGROUND

Idiopathic thrombocytopenic purpura (ITP), also known as primary immune thrombocytopenia, is an autoimmune disorder characterized by isolated thrombocytopenia (peripheral blood platelet count less than $100 \times 10^9$/L) in the absence of other causes or disorders that may be associated with thrombocytopenia. Rodeghiero et al., *Blood*, 113(11): 2386-2393 (2009). The underlying pathophysiology of ITP has traditionally been attributed to increased rates of destruction of antibody-coated platelets. In addition, impaired platelet production has emerged as an important mechanism contributing to the thrombocytopenia of ITP. The clinical manifestations of ITP are highly variable with a spectrum ranging from no symptoms to catastrophic hemorrhage. Symptoms are largely, though not exclusively, related to platelet count. Rodeghiero et al., *Blood*, 113(11): 2386-2393 (2009).

The first-line treatment of patients presenting with ITP comprises oral or intravenous corticosteroids (prednisone is steroid most frequently used). Following initial response, relapse is common when the dose is reduced. George et al., *Blood*, 88(1):3-40 (1996). Long-term responses are seen in only around 20-30% patients. Provan et al., *Blood*, 115:168-186 (2010). Early management of those unresponsive to steroids includes intravenous immunoglobulins (IVIg), associated with response in about 80% cases. Newman et al., *Br. J. Haematol.*, 112(4):1076-1078 (2001). However, the platelet counts often drift back to pre-treatment levels within 3-4 weeks. Treatment of patients with chronic ITP who fail first-line therapy is extremely challenging. Provan et al., *Blood*, 115:168-186 (2010). Chances of inducing a durable and complete response are low in these patients; therefore, the goals of therapy are to provide a "safe" platelet count to prevent major (including potentially fatal) bleeding while minimizing treatment-related side effects. Splenectomy is the only curative treatment modality and two-thirds of patients who undergo splenectomy will achieve a normal platelet count which is often sustained with no additional therapy. Ghanima et al., *Blood*, 120(5):960-969 (2012). There is no consensus regarding the optimal time for performing splenectomy, or for predicting response and the long-term effectiveness of splenectomy. In about 30% of patients, splenectomy fails to induce a satisfactory response and these patients require additional treatment. Cuker et al., *Hematol. Am. Soc. Hematol. Educ. Program* 2010, 377-384 (2010).

Current ITP treatments work in a variable fraction of patients and prediction of efficacy is impossible. Moreover, ITP treatments (e.g., corticosteroids) address the destruction component of the disease, without addressing underlying cause. Most therapies (including splenectomy) for long-term chronic use have significant tolerability issues, generally associated with immunosuppression, and for some agents, even mortality. Few of the agents have been tested in controlled clinical trials and none have demonstrated a significant reduction in the bleeding associated with the low platelet counts. The vast majority of drugs are prescribed off-label (e.g., azathioprine, danazol, vinca alkaloids and rituximab), and have variable and often only transient efficacy in patients with chronic ITP. Neunert et al., *Blood*, 117(16):4190-4207 (2011). The day to day clinical management of patients with chronic ITP is therefore, a significant problem.

The crucial role of CD40-CD40L interactions in immune and inflammatory responses has made them a promising target for treatment of pathological immuno-inflammatory processes. Blockade of CD40-CD40L interactions by means of specific CD40L monoclonal antibodies (mAbs) successfully prevents allograft rejection in primates and treats autoimmune diseases and atherosclerosis in animal models. Montgomery et al., *Transplantation*, 74:1365-1369 (2002). In humans, two different anti-CD40L mAb clones have been used in clinical trials for treatment of different autoimmune diseases. Maribel et al., *Mol. Immunol.*, 45:937-944 (2008). Monoclonal antibodies, however, can display unusually high incidence of thromboembolic (TE) complications, such as atherothrombotic central nervous system events, myocardial infarction, pulmonary embolism, and deep vein thrombosis. For example, the usefulness of the anti-CD40L mAb clone hu5c8 (anti-CD40L mAb, Biogen) is limited by an unusually high incidence of TE complications. TE by these antibodies is thought to result from the formation of higher-order immune complexes (IC) of the mAbs with membrane-bound CD40L on platelets, or sCD40L shed from platelets, that can ligate and thereby aggregate neighboring platelets via their FcgRIIa receptors, resulting in thrombi formation. The risk of thromboembolism has led to a halt in all ongoing clinical trials. Boumpas et al., *Arthritis Rheum.*, 48:719-727 (2003).

Accordingly, it is an object of this invention to provide improved methods for treating subjects with ITP and other autoimmune disorders without the risk of thromboembolism.

SUMMARY

In certain aspects, the present invention relates to use of antibody polypeptides that specifically bind and inhibit human CD40L (also referred to as "anti-CD40L antibody polypeptides") and that are useful in the treatment of diseases involving CD40L activation are disclosed. The antibody polypeptides advantageously do not cause platelet aggregation. Ultimately, targeting CD40L with the antibody polypeptide can provide opportunity to inhibit autoimmune processes leading to, for example, primary immune thrombocytopenia, solid organ transplant rejection, graft-related disease, pemphigus vulgaris, systemic sclerosis, and myasthenia gravis and induce durable disease remission. The antibody polypeptide can thus provide long lasting therapeutic benefits for autoimmune disease patients. The antibody polypeptide thus offers a novel therapeutic modality, currently not available to patients. Given the lack of therapeutic options for autoimmune disease subjects who have failed all conventional therapies, the antibody polypeptide with its distinct mechanism of action and known safety profile demonstrates a favorable Risk/Benefit profile.

Unmet medical need for ITP in particular includes: 1) management of severe, chronic ITP in patients who are intolerant of (due to treatment-associated side effects) or inappropriate for (due to comorbidities) treatment with non-selective immunosuppressive agents or refractory to available treatment options (including splenectomy), where the life-threatening bleeding risk remains high and quality of life decreases; 2) more effective and safer therapies, potentially curative and/or inducing long lasting remission (focusing on reducing PLT destruction) and able to reduce or eliminate need for CS and replace or significantly defer splenectomy.

A pharmaceutical composition is provided comprising a therapeutically-effective amount of the anti-CD40L antibody polypeptide and a pharmaceutically acceptable carrier. The pharmaceutical composition can further comprise an immunosuppressive/immunomodulatory and/or anti-inflammatory agent.

In certain embodiments, a method of treating an immune disease in a patient in need of such treatment is provided. Such method comprises administering to the patient a therapeutically effective amount of the anti-CD40L antibody polypeptide described herein. The immune disease can be an autoimmune disease or a graft-related disease. The immune disease can be selected from the group consisting of selected from the group consisting of Addison's disease, allergies, ankylosing spondylitis, asthma, atherosclerosis, autoimmune diseases of the ear, autoimmune diseases of the eye, autoimmune hepatitis, autoimmune parotitis, colitis, coronary heart disease, Crohn's disease, diabetes, including Type 1 and/or Type 2 diabetes, epididymitis, glomerulonephritis, graft-related disease, Graves' disease, Guillain-Barre syndrome, Hashimoto's disease, hemolytic anemia, idiopathic thrombocytopenic purpura (also known as primary immune thrombocytopenia), inflammatory bowel disease, immune response to recombinant drug products (e.g., Factor VII in hemophiliacs), systemic lupus erythematosus, male infertility, multiple sclerosis, myasthenia gravis, pemphigus (such as pemphigus vulgaris and pemphigus foliaceus), psoriasis, rheumatic fever, rheumatoid arthritis, sarcoidosis, scleroderma (systemic sclerosis), Sjogren's syndrome, spondyloarthropathies, thyroiditis, transplant rejection, and vasculitis. Autoimmune-mediated conditions include, but are not limited to, conditions in which the tissue affected is the primary target, and in some cases, the secondary target. Such conditions include, but are not limited to, AIDS, atopic allergy, bronchial asthma, eczema, leprosy, schizophrenia, inherited depression, transplantation of tissues and organs (such as solid organ transplant), chronic fatigue syndrome, Alzheimer's disease, Parkinson's disease, myocardial infarction, stroke, autism, epilepsy, Arthus' phenomenon, anaphylaxis, alcohol addiction, and drug addiction. Furthermore, the graft-related disease can comprise solid organ, tissue and/or cell transplant rejection. Alternatively, the graft-related disease is graft versus host disease (GVHD). The graft-related disease can further be an acute transplant rejection. Alternatively, the graft-related disease can be a chronic transplant rejection. In a specific embodiment, the autoimmune disease is idiopathic thrombocytopenic purpura (ITP).

Also provided is a method of treating an immune disease in a patient, the method comprising administering to the patient a therapeutically-effective amount of an anti-CD40L antibody polypeptide (e.g., BMS-986004), wherein at least one dose of the antibody polypeptide is administered at a dose from about 75 mg to about 1500 mg. The dose can be at least about 75 mg, at least about 225 mg, or at least about 675 mg. The dose can be about 75 mg, about 225 mg, about 675 mg, or about 1500 mg. Alternatively, the dose may range from about 200 mg to about 1200 mg, or from about 500 mg to about 1000 mg. Optionally, the method comprises at least one administration cycle (e.g., 2 weeks).

The antibody polypeptide can be formulated in a pharmaceutical composition for intravenous administration. The pharmaceutical composition can comprise a pharmaceutically acceptable carrier. For example, the pharmaceutical composition comprises 10 mM sodium phosphate, pH 6.5, 25 mM arginine HCl, and 250 mM sucrose.

The antibody polypeptide can be administered intravenously. The dose of antibody polypeptide may be from about 200 to about 1500 mg. At least 2 doses can be administered. Optionally, at least 7 doses can be administered. When multiple doses are administered, the doses may be the same or different. The dose can be administered once every 2 weeks.

The method can normalize platelet counts in the patient. Optionally, the patient's baseline peripheral blood platelet count can at least double after treatment. The patient's peripheral blood baseline platelet count can be greater than or equal to 50,000/mm$^3$ or greater than or equal to 100,000/mm$^3$ after treatment. The patient can demonstrate a peripheral blood platelet count increase of 20,000/mm$^3$ after treatment. The patient can have a peripheral blood platelet count of less than 30,000/mm$^3$ before treatment. The patient can have a peripheral blood platelet count of less than 100×10$^9$ L or 50×10$^9$ L before treatment. The patient can be splenectomized prior to treatment. Optionally, the patient was previously treated for ITP before treatment. Alternatively, the patient was not previously treated for ITP before treatment.

In certain embodiments, the methods of the present invention further comprise administering to patient an immunosuppressive/immunomodulatory and/or anti-inflammatory agent. The immunosuppressive/immunomodulatory and/or anti-inflammatory agent and the anti-CD40L antibody polypeptide may be administered sequentially or concurrently.

A kit for treating an immune disease in a patient is also provided, the kit comprising: (a) a dose of an anti-CD40L antibody polypeptide (e.g., BMS-986004); and (b) instructions for using the antibody polypeptide.

Also provided is an anti-CD40L antibody polypeptide (e.g., BMS-986004) for administration, wherein at least one dose of the anti-CD40L antibody polypeptide is administered at a dose of about 75 to about 1500 mg.

Also provided is a use of an anti-CD40L antibody polypeptide disclosed herein for the preparation of a medicament for the treatment of a patient, wherein the patient has or is at risk of having an immune disease. Further provided is a use of an anti-CD40L antibody polypeptide disclosed herein for preparation of a medicament for alleviating at least one symptom of an immune disease in a patient in need thereof. Further provided is an anti-CD40L antibody polypeptide (e.g., BMS-986004) for use in at least one administration cycle, wherein for each cycle one dose of the antibody polypeptide is administered at a dose of about 75 to about 1500 mg.

The anti-CD40L antibody polypeptides comprise a variable domain. Exemplary antibody polypeptides are in the form of a domain antibody (dAb) that contains a single variable domain. Alternatively, the dAbs can be bi-specific reagents that comprise a second variable domain that can bind another antigen, such as human serum albumin (HSA), for example.

In certain embodiments, the antibody polypeptide of the invention comprises a first variable domain that specifically binds human CD40L, wherein CD40L comprises the amino acid sequence of SEQ ID NO: 1, wherein the amino acid sequence of the first variable domain comprises: (a) a CDR1 region which differs from the CDR1 region of BMS2h-572-633 (SEQ ID NO: 2) by up to three amino acids, (b) a CDR2 region which differs from the CDR2 region of BMS2h-572-633 ((SEQ ID NO: 3) by up to three amino acids, (c) a CDR3 region which differs from the CDR3 region of BMS2h-572-633 (SEQ ID NO: 4) by up to three amino acids; and wherein the antibody polypeptide inhibits binding of CD40L to CD40 with an EC50 of 100 pM to 100 nM. Alternatively, the amino acid sequence of the first variable domain can differ from the amino acid sequence of BMS2h-572-633 (SEQ ID NO: 5) by up to and including 10 amino acids. Furthermore, the amino acid sequence of the first variable domain can differ from SEQ ID NO: 5 by up to and including 5 amino acids. The amino acid sequence of the first variable domain can also differ from SEQ ID NO: 5 by up to and including 2 amino acids. Alternatively, the first variable domain differs from SEQ ID NO: 5 by 1 amino acid. Alternatively, the variable domain of the antibody polypeptide comprises an amino acid sequence that is at least 95%, 96%, 97%, 98%, 99% or 100% identical to SEQ ID NO: 5.

In certain specific embodiments, the variable domain of the antibody polypeptide comprises: (1) a CDR1 region having the amino acid sequence of SEQ ID NO: 2; (2) a CDR2 region having the amino acid sequence of SEQ ID NO: 3; and (1) a CDR3 region having the amino acid sequence of SEQ ID NO: 4. For example, the variable domain of the antibody polypeptide comprises the amino acid sequence of SEQ ID NO: 5 (BMS2h-572-633). Preferably, the antibody polypeptide is BMS-986004 and comprises the amino acid sequence of SEQ ID NO: 6.

Also provided is an antibody polypeptide comprising a first variable domain that specifically binds human CD40L, wherein the antibody polypeptide is a domain antibody (dAb). The antibody polypeptide can be a fusion polypeptide comprising the first variable domain and an Fc domain. Alternatively, the fusion polypeptide can comprise an IgG4 Fc domain. The fusion polypeptide also can comprise an IgG1 Fc domain. The fusion polypeptide can also comprise an IgG1 Fc domain. Alternatively, the fusion polypeptide can comprise a CT-Long domain. The fusion polypeptide can also comprise a CT-short domain. Alternatively, the fusion polypeptide can comprise a N297Q Long Fc domain. The fusion polypeptide can alternatively comprise a N297Q Short Fc domain.

Also provided is an antibody polypeptide comprising a first variable domain that specifically binds human CD40L, wherein the antibody polypeptide further comprises a second variable domain that specifically binds a second antigen, wherein the second antigen is an antigen other than human CD40L. The second antigen can be a cluster of differentiation (CD) molecule or a Major Histocompatibility Complex (MHC) Class II molecule. Alternatively, the second antigen can be serum albumin (SA).

BRIEF DESCRIPTION OF THE FIGURES

FIG. 1B shows the amino acid sequence of BMS-986004 (SEQ ID NO: 6). BMS-986004 is an Fc fusion protein comprising the variable domain of BMS2h-572-633 (SEQ ID NO: 5) and a modified Fc tail from Abatacept IgG1. The Fc fusion protein is a dimer of molecular weight 77,984 Daltons, with each polypeptide chain consisting of 353 amino acids. The variable domain is fused by a linker (residues "AST" underlined) to the mutated Fc construct of human IgG1, wherein three cysteine residues (the first three underlined "S" residues) are substituted with serine, and one proline (the last underlined "S" residue) is substituted with a serine residue.

DETAILED DESCRIPTION

Figure 1A:
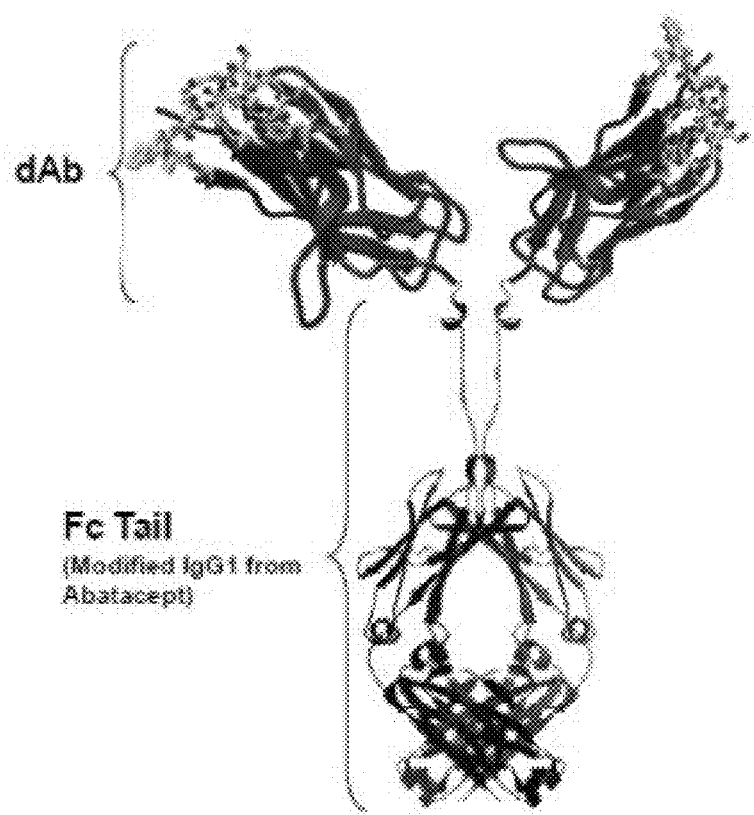
FIG. 1A depicts the domain antibody that comprises a $V_H$ variable domain BMS2h-572-633 fused to a modified Fc tail from Abatacept IgG1.

The present invention provides methods of treating autoimmune diseases (e.g., primary immune thrombocytopenia) using antibody polypeptides that specifically bind to human CD40L. The antibody polypeptides do not activate platelets, and the antibody polypeptides are useful in the treatment of diseases involving CD40L activation, such as graft-related diseases and autoimmune diseases.

An "anti-CD40L antibody polypeptide" and "antibody polypeptide" are used interchangeably herein. In one aspect, the antibody polypeptides may be a domain antibody containing a single variable domain. The antibody polypeptides also may comprise additional domains, such as an Fc domain. For instance, the antibody polypeptide may comprise a second variable domain that specifically binds human serum albumin (HSA). Such dual specific antibody polypeptides may have an increased half-life, for example. In a specific embodiment, the antibody polypeptide comprises a variable domain of the dAb BMS2h-572-633. In another specific embodiment, the antibody polypeptide competes with the binding of the dAb BMS2h-572-633.

A "fixed dose" is a dose administered regardless of the subjects' body weight.

A "therapeutically effective amount" refers to an amount (at dosages and for periods of time and for the means of administration) to achieve a desired therapeutic result.

As used herein, "specific binding" refers to the binding of an antigen by an antibody polypeptide with a dissociation constant ($K_d$) of about 1 μM or lower as measured, for example, by surface plasmon resonance (SPR). Suitable assay systems include the BIACORE® surface plasmon resonance system and BIACORE® kinetic evaluation software (e.g., version 2.1). The affinity or $K_d$ for a specific binding interaction may be about 1 μM or lower, about 500 nM or lower or about 300 nM or lower.

The term "about" will be understood by persons of ordinary skill in the art and will vary to some extent on the context in which it is used. Generally, about encompasses a range of values that are plus/minus 10% of a referenced value.

In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

1. CD40L and CD40L Activities

Antibody polypeptides are provided that bind human CD40L. CD40L is also known as CD154, gp39, TNF-related activation protein (TRAP), 5c8 antigen, or T-BAM. Relevant structural information for human CD40L can be found, for example, at UniProt Accession Number P29965. "Human CD40L" refers to the CD40L comprising the following amino acid sequence:

```
                                            (SEQ ID NO: 1)
          10         20         30         40
    MIETYNQTSP RSAATGLPIS MKIFMYLLTV FLITQMIGSA 50         60         70         80
    LFAVYLHRRL DKIEDERNLH EDFVFMKTIQ RCNTGERSLS 90        100        110        120
    LLNCEEIKSQ FEGFVKDIML NKEETKKENS FEMQKGDQNP 130        140        150        160
    QIAAHVISEA SSKTTSVLQW AEKGYYTMSN NLVTLENGKQ 170        180        190        200
    LTVKRQGLYY IYAQVTFCSN REASSQAPFI ASLCLKSPGR 210        220        230        240
    FERILLRAAN THSSAKPCGQ QSIHLGGVFE LQPGASVFVN 250        260
    VTDPSQVSHG TGFTSFGLLK L
```

Binding of the present antibody polypeptides to CD40L antagonizes CD40L activity. "CD40L activities" include, but are not limited to, costimulation and activation an APC in association with T cell receptor stimulation by MHC molecules on the APC, secretion of all immunoglobulin isotypes in the presence of cytokines, stimulation of B cell proliferation, cytokine production, antibody class switching and affinity maturation. For example, patients with X-linked hyper-IgM syndrome express functional CD40 on their B cells, but their activated T cells have a defective CD40L protein, resulting in its inability to activate B cells and induce immunoglobulin isotype switching. Aruffo et al., *Cell*, 72:291-300 (1993).

CD40L activities can be mediated by interaction with other molecules. "CD40 activities" include the functional interaction between CD40L and the following molecules: CD40 (CD40L receptor), α5β1 integrin, and αIIbβ3. For example, CD40L binds its receptor, CD40, which is expressed on a variety of APCs, such as B cells, macrophages, and dendritic cells, as well as on stromal cells, vascular endothelial cells, and platelets.

As used herein, the terms "activate", "activates", and "activated" refer to an increase in a given measurable CD40L activity by at least 10% relative to a reference, for example, at least 10%, 25%, 50%, 75%, or even 100%, or more. A CD40L activity is "antagonized" if the activity is reduced by at least 10%, and in an exemplary embodiment, at least 20%, 30%, 40%, 50%, 60%, 70%, 80%, 90%, 95%, 97%, or even 100% (i.e., no detectable activity), relative to the absence of the antagonist. For example, an antibody polypeptide may antagonize some or all CD40L activity. In one embodiment, the antibody polypeptide does not activate B cell proliferation. In another embodiment, the antibody polypeptide does not activate cytokine secretion by T cells or dendritic cells (DCs), where the cytokine is at least one cytokine selected from the group consisting of IL-2, IL-6, IL-10, IL-12, IL-13, IL-17, IL-23, TNF-α, and IFN-γ.

2. Antibody Polypeptides

The antibody polypeptides comprise a variable domain. In one embodiment, the antibody polypeptides are in the form of a dAb that contains a single variable domain. Antibody polypeptides may be full-length anti-CD40L immunoglobulin molecules comprising two heavy (H) chains and two light (L) chains interconnected by disulfide bonds. In this embodiment, the amino terminal portion of each chain includes a variable domain ($V_L$ or $V_H$) of about 100-120 amino acids. The complementarity determining regions (CDRs) contained therein are primarily responsible for antigen recognition, although framework residues can play a role in epitope binding. The carboxy-terminal "half" of each heavy chain defines a constant region (Fc) primarily responsible for effector function.

Antibody polypeptides also may be "fragments" comprising a portion of the full-length anti-CD40L immunoglobulin molecule that comprises a variable domain that specifically binds CD40L. Thus, the term "antibody polypeptides" includes an antigen-binding heavy chain, light chain, heavy chain-light chain dimer, Fab fragment, F(ab')2 fragment, Fv fragment, single chain Fv (scFv), and dAb, for example. The term "antibody polypeptides" thus includes polypeptides made by recombinant engineering and expression, as well as monoclonal antibodies produced by natural recombination and secretion by hybridoma cell clones.

Light chains are classified as kappa (κ) or lambda (λ), and are characterized by a particular constant region, $C_L$, as known in the art. Heavy chains are classified as γ, μ, α, δ, or ε, and define the isotype of an antibody as IgG, IgM, IgA, IgD, or IgE, respectively. The heavy chain constant region is comprised of three domains (CH1, CH2, and CH3) for IgG, IgD, and IgA; and four domains (CH1, CH2, CH3, and CH4) for IgM and IgE. Anti-CD40L antibodies may have a heavy chain constant region selected from any of the immunoglobulin classes (IgA, IgD, IgG, IgM, and IgE).

Each light chain variable domain ($V_L$) and heavy chain variable domain ($V_H$) is composed of three CDRs and four framework regions (FRs), arranged from amino-terminus to carboxy-terminus in the following order: FR1, CDR1, FR2, CDR2, FR3, CDR3, and FR4. The three CDRs of the light chain are referred to as "LCDR1, LCDR2, and LCDR3" and the three CDRs of the heavy chain are referred to as "HCDR1, HCDR2, and HCDR3".

As used herein, the term "Fc domain" refers to the constant region antibody sequences comprising CH2 and CH3 constant domains as delimited according to Kabat et al., *Sequences of Immunological Interest*, Fifth Edition, U.S. Dept. Health & Human Services, Washington, D.C. (1991). The Fc domain may be derived from an IgG1 or an IgG4 Fc region, for example.

A variable domain may be fused to an Fc domain. When a variable domain is fused to an Fc domain, the carboxyl terminus of the variable domain (either a $V_L$ or $V_H$ domain, including dAbs) may be linked or fused to the amino terminus of the Fc CH2 domain. Alternatively, the carboxyl terminus of the variable domain may be linked or fused to the amino terminus of a CH1 domain, which itself is fused to the Fc CH2 domain. The protein may comprise the hinge region between the CH1 and CH2 domains in whole or in part.

The CDRs contain most of the residues that form specific interactions with the antigen. In one embodiment, the variable domain of an antibody polypeptide comprises CDR1, CDR2, and CDR3 regions of that have the same amino acid sequence as the CDR1, CDR2, and CDR3 regions of BMS2h-572-633 or that each differ from the CDR1, CDR2, and CDR3 regions of BMS2h-572-633 by one, two, or three amino acids.

In certain specific embodiments, the variable domain of the antibody polypeptide comprises: (1) a CDR1 region having the amino acid sequence of SEQ ID NO: 2; (2) a CDR2 region having the amino acid sequence of SEQ ID NO: 3; and (1) a CDR3 region having the amino acid sequence of SEQ ID NO: 4.

A "domain antibody" (dAb) comprises a single variable ($V_L$ or $V_H$) domain that is capable of specifically and monovalently binding an antigen, such as CD40L. For example, a dAb may have a $V_{HH}$ structure, characteristic of a camelid dAb. A "$V_H$ domain" as used herein is meant to include a $V_{HH}$ structure. In another embodiment, the $V_H$ domains (including all features and combination of features presented as embodiments herein) are other than $V_{HH}$ domains. dAbs may form homo- or heterodimers in solution. While not limited by any particular theory, it is believed that the dAbs disclosed herein do not cause platelet aggregation, because the antibodies containing mutated Fc constructs do not bind FcγRIIa (also known as CD32a) on the platelet surface and do not activate platelets.

In a specific embodiment, the invention provides use of the anti-CD40L VH dAb BMS2h-572-633. The amino acid sequence of BMS2h-572-633 (SEQ ID NO: 5) is shown below, comprising the CDR1 sequence (WELMG; SEQ ID NO: 2); the CDR2 sequence (GIEGPGDVTYYADSVKG; SEQ ID NO: 3), and the CDR3 sequence (KDAKSDY; SEQ ID NO: 4).

BMS2h-572-633 (SEQ ID NO: 5; CDR1-3 regions are underlined):

```
EVQLLESGGG LVQPGGSLRL SCAASGFTFN WELMGWARQA

PGKGLEWVSG IEGPGDVTYY ADSVKGRFTI SRDNSKNTLY

LQMNSLRAED TAVYYCVKVG KDAKSDYRGQ GTLVTVSS
```

As used herein, the term "variable domain" refers to immunoglobulin variable domains defined by Kabat et al., *Sequences of Immunological Interest*, Fifth Edition, U.S. Dept. Health & Human Services, Washington, D.C. (1991). The numbering and positioning of CDR amino acid residues within the variable domains is in accordance with the well-known Kabat numbering convention.

The term "human", when applied to antibody polypeptides, means that the antibody polypeptide has a sequence, e.g., framework regions and/or CH domains, derived from a human immunoglobulin. A sequence is "derived from" a human immunoglobulin coding sequence when the sequence is either: (a) isolated from a human individual or from a cell or cell line from a human individual; (b) isolated from a library of cloned human antibody gene sequences or of human antibody variable domain sequences; or (c) diversified by mutation and selection from one or more of the polypeptides above. An "isolated" compound as used herein means that the compound is removed from at least one component with which the compound is naturally associated with in nature.

Antibody polypeptides can be administered to patients while largely avoiding the anti-antibody immune response often provoked by the administration of antibodies from other species, e.g., mouse. For example, murine antibodies can be "humanized" by grafting murine CDRs onto a human variable domain FR, according to procedures well known in the art. Human antibodies as disclosed herein, however, can be produced without the need for genetic manipulation of a murine antibody sequence.

Variable domains may comprise one or more FR with the same amino acid sequence as a corresponding framework region encoded by a human germline antibody gene segment. For example, a domain antibody may comprise the $V_H$ germline gene segments DP47, DP45, or DP38, the $V_K$ germline gene segment DPK9, the JH segment JH4b, or the $J_K$ segment $J_K1$.

Changes may be made to antibody polypeptide sequences while retaining the ability to bind CD40L specifically. Specifically, the antibody polypeptides (e.g., a dAb) may comprise a variant variable domain that retains the function of specifically binding CD40L as the dAb BMS2h-572-633. In one embodiment, the variant variable domain may compete with BMS2h-572-633 for specific binding to CD40L. Error-prone affinity maturation, as disclosed in the examples below, provides one exemplary method for making and identifying antibody polypeptides with variant sequences that specifically bind CD40L.

In certain embodiments, a variant variable domain may differ from the variable domain of BMS2h-572-633 (SEQ ID NO: 5) by up to 10 amino acids or any integral value between, where the variant variable domain specifically binds CD40L. Alternatively, the variant variable domain may have at least 90% sequence identity (e.g., at least 91%, 92%, 93%, 94%, 95%, 96%, 97%, 98%, or 99% sequence identity) relative to a sequence listed in the present Sequence Listing. Non-identical amino acid residues or amino acids that differ between two sequences may represent amino acid substitutions, additions, or deletions. Residues that differ between two sequences appear as non-identical positions, when the two sequences are aligned by any appropriate amino acid sequence alignment algorithm, such as BLAST[SM].

In a specific embodiment, the variable domain of the antibody polypeptide comprises the amino acid sequence of SEQ ID NO: 5 (BMS2h-572-633). Preferably, the antibody polypeptide is BMS-986004 and comprises the amino acid sequence of SEQ ID NO: 6.

The information regarding the boundaries of the $V_L$ or $V_H$ domains of heavy and light chain genes may be used to design PCR primers to amplify the variable domain from a cloned heavy or light chain coding sequence encoding an antibody polypeptide known to bind CD40L. The amplified variable domain may be inserted into a suitable expression vector, e.g., pHEN-1 (Hoogenboom et al., *Nucleic Acids Res.* 19:4133-4137 (1991)) and expressed, either alone or as a fusion with another polypeptide sequence, using techniques well known in the art. Based on the disclosed amino acid and polynucleotide sequences, the fusion protein can be produced and purified using only ordinary skill in any suitable mammalian host cell line, such as CHO, 293, COS, NS0, and the like, followed by purification using one or a combination of methods, including protein A affinity chromatography, ion exchange, reverse phase techniques, or the like.

In one aspect, the antibody polypeptide is a "dual specific" antibody polypeptide comprising a first variable domain that specifically binds human CD40L. Dual specific antibody polypeptides comprise a second variable domain that specifically binds a second antigen that is other than human CD40L.

In another embodiment, the second antigen may be a cell surface molecule of an immune effector cell or a soluble molecule such as a cytokine, for example. Binding of the dual specificity antibody polypeptide could be used to antagonize CD40L and antagonize a biological activity of the second antigen. Cell surface molecules of immune effector cells include the cluster of differentiation (CD) molecules. Representative CD markers are listed on the Internet at hypertext transfer protocol http://en.wikipedia.org/wiki/List_of_human_clusters_of_differentiation (last modified on Aug. 8, 2012). Cell surface molecules of immune effector cells also include Major Histocompatibility Complex (MHC) Class II molecules. Antibodies against these cell surface molecules are known in the art and can be used a source of a variable domain to construct a dual specific antibody polypeptide.

In one embodiment, antibody polypeptides of a dual specific ligand may be linked by an "amino acid linker" or "linker". For example, a dAb may be fused to the N-terminus of an amino acid linker, and another dAb may be fused to the C-terminus of the linker. Although amino acid linkers can be any length and consist of any combination of amino acids, the linker length may be relatively short (e.g., five or fewer amino acids) to reduce interactions between the linked domains. The amino acid composition of the linker also may be adjusted to reduce the number of amino acids with bulky side chains or amino acids likely to introduce secondary structure. Suitable amino acid linkers include, but are not limited to, those up to 3, 4, 5, 6, 7, 10, 15, 20, or 25 amino acids in length.

The binding of the second antigen can increase the in vivo half-life of the antibody polypeptide. For example, the second variable domain of the dual specific antibody polypeptide may specifically bind serum albumin (SA), e.g., human serum albumin (HSA). The antibody polypeptide formatted to bind I can have an increased in vivo t-α ("alpha half-life") or t-β ("beta half-life") half-life relative to the same unformatted antibody polypeptide. The t-α and t-β half-lives measure how quickly a substance is distributed in and eliminated from the body. The linkage to I may be accomplished by fusion of the antibody polypeptide with a second variable domain capable of specifically binding I, for example. Anti-human serum albumin antibodies are well-known in the art. See, e.g., Abcam, Human Serum Albumin antibodies ab10241, ab2406, and ab8940, available on the Internet at hypertext transfer protocol www.abcam.com/index.html, or GenWay, ALB antibody, available on the Internet at hypertext transfer protocol www.genwaybio.com. Variable domains that specifically bind I can be obtained from any of these antibodies, and then fused to an antibody polypeptide of the disclosure using recombinant techniques that are well known in the art.

Alternatively, the linking of the antibody polypeptide to I can be accomplished by directly fusing the antibody polypeptide sequence to an I coding sequence using techniques well known to the skilled artisan. The I coding sequences can be obtained by PCR using primers derived from the cDNA sequence available at GENBANK® Accession No. NM000477, for example.

In one embodiment, the ta-half-life of the I-linked domain antibody composition is increased by 10% or more. In another embodiment, the tα-half-life of the I-linked domain antibody composition is in the range of 0.25 hours to 6 hours. In another embodiment, the tβ-half-life of the I-linked domain antibody composition is increased by 10% or more. In another embodiment, the tβ-half-life of the I-linked domain antibody composition is in the range of 12 to 48 hours.

In another embodiment, an antibody polypeptide may be formatted to increase its in vivo half-life by PEGylation. In one embodiment, the PEG is covalently linked. In another embodiment, the PEG is linked to the antibody polypeptide at a cysteine or lysine residue. In yet another embodiment, the PEG-linked antibody polypeptide has a hydrodynamic size of at least 24 kD. In yet another embodiment, the total PEG size is from 20 to 60 kD, inclusive. In yet another embodiment, the PEG-linked domain antibody has a hydrodynamic size of at least 200 kD.

PEGylation can be achieved using several PEG attachment moieties including, but not limited to N-hydroxysuccinimide active ester, succinimidyl propionate, maleimide, vinyl sulfone, or thiol. A PEG polymer can be linked to an antibody polypeptide at either a predetermined position, or can be randomly linked to the domain antibody molecule. PEGylation can also be mediated through a peptide linker attached to a domain antibody. That is, the PEG moiety can be attached to a peptide linker fused to an antibody polypeptide, where the linker provides the site (e.g., a free cysteine or lysine) for PEG attachment. Methods of PEGylating antibodies are well known in the art, as disclosed in Chapman et al., "PEGylated antibodies and antibody fragments for improved therapy: a review", Adv. Drug Deliv. Rev., 54(4):531-545 (2002), for example.

Antibody polypeptides also may be designed to form a dimer, trimer, tetramer, or other multimer. Antibody polypeptides, e.g., dAbs, can be linked to form a multimer by several methods known in the art, including, but not limited to, expression of monomers as a fusion protein, linkage of two or more monomers via a peptide linker between monomers, or by chemically joining monomers after translation, either to each other directly, or through a linker by disulfide bonds, or by linkage to a di-, tri- or multivalent linking moiety (e.g., a multi-arm PEG). In one embodiment, the multimer can bind a single molecule of CD40.

3. Pharmaceutical Compositions and Methods of Treatment

In certain embodiments, the present invention provides a pharmaceutical composition for treating an immune disease, comprising a therapeutically-effective amount of an anti-CD40L antibody polypeptide and a pharmaceutically acceptable carrier. Pharmaceutically acceptable carriers include, for example, water, saline, phosphate buffered saline, dextrose, glycerol, ethanol and the like, as well as combinations thereof. Pharmaceutically acceptable carriers can further comprise minor amounts of auxiliary substances, such as wetting or emulsifying agents, preservatives, or buffers that enhance the shelf-life or effectiveness of the fusion protein. The compositions can be formulated to provide quick, sustained, or delayed release of the active ingredient(s) after administration. Suitable pharmaceutical compositions and processes for preparing them are well known in the art. See, e.g., Remington, The Science and Practice of Pharmacy, 21st Edition, Gennaro, A. et al., eds., Mack Publishing Company (2005).

The pharmaceutical composition may further comprise an immunosuppressive/immunomodulatory and/or anti-inflammatory agent. A method of treating an immune disease in a patient in need of such treatment may comprise administering to the patient a therapeutically effective amount of the pharmaceutical composition. Antagonizing CD40L-mediated T cell activation could inhibit undesired T cell responses occurring during autoimmunity, transplant rejection, or allergic responses, for example. Inhibiting CD40L-mediated T cell activation could moderate the progression and/or severity of these diseases.

As used herein, a "patient" means an animal, e.g., mammal, including humans. The patient may be diagnosed with an immune disease. "Treatment" or "treat" or "treating"

refers to the process involving alleviating the progression or severity of a symptom, disorder, condition, or disease. An "immune disease" refers to any disease associated with the development of an immune reaction in an individual, including a cellular and/or a humoral immune reaction. Examples of immune diseases include, but are not limited to, graft-related disease, inflammation, allergy, and autoimmune disease. The autoimmune disease may be selected from the group consisting of idiopathic thrombocytopenic purpura (ITP), systemic lupus erythematosus, multiple sclerosis, rheumatoid arthritis, diabetes, psoriasis, scleroderma, atherosclerosis, inflammatory bowel disease, and ulcerative colitis.

Diseases that can be treated by administering the pharmaceutical composition may be selected from the group consisting of Addison's disease, allergies, ankylosing spondylitis, asthma, atherosclerosis, autoimmune diseases of the ear, autoimmune diseases of the eye, autoimmune hepatitis, autoimmune parotitis, colitis, coronary heart disease, Crohn's disease, diabetes, including Type 1 and/or Type 2 diabetes, epididymitis, glomerulonephritis, graft-related disease, Graves' disease, Guillain-Barre syndrome, Hashimoto's disease, hemolytic anemia, idiopathic thrombocytopenic purpura (also known as primary immune thrombocytopenia), inflammatory bowel disease, immune response to recombinant drug products (e.g., Factor VII in hemophiliacs), systemic lupus erythematosus, male infertility, multiple sclerosis, myasthenia gravis, pemphigus (such as pemphigus vulgaris and pemphigus foliaceus), psoriasis, rheumatic fever, rheumatoid arthritis, sarcoidosis, scleroderma (systemic sclerosis), Sjogren's syndrome, spondyloarthropathies, thyroiditis, transplant rejection, and vasculitis. Autoimmune-mediated conditions include, but are not limited to, conditions in which the tissue affected is the primary target, and in some cases, the secondary target. Such conditions include, but are not limited to, AIDS, atopic allergy, bronchial asthma, eczema, leprosy, schizophrenia, inherited depression, transplantation of tissues and organs (such as solid organ transplant), chronic fatigue syndrome, Alzheimer's disease, Parkinson's disease, myocardial infarction, stroke, autism, epilepsy, Arthus' phenomenon, anaphylaxis, alcohol addiction, and drug addiction.

In certain specific embodiments, the present invention provides methods of treating idiopathic thrombocytopenic purpura (ITP) using an anti-CD40L antibody polypeptide (such as BMS-986004). The method can normalize platelet counts in the patient. Optionally, the patient's baseline peripheral blood platelet count can at least double after treatment. The patient's peripheral blood baseline platelet count can be greater than or equal to 50,000/mm$^3$ or greater than or equal to 100,000/mm$^3$ after treatment. The patient can demonstrate a peripheral blood platelet count increase of 20,000/mm$^3$ after treatment. The patient can have a peripheral blood platelet count of less than 30,000/mm$^3$ before treatment. The patient can have a peripheral blood platelet count of less than 100×10$^9$ L or 50×10$^9$ L before treatment. The patient can be splenectomized prior to treatment. Optionally, the patient was previously treated for ITP before treatment. Alternatively, the patient was not previously treated for ITP before treatment.

The pharmaceutical composition may be administered alone or in combination therapy, (i.e., simultaneously or sequentially) with an immunosuppressive/immunomodulatory and/or anti-inflammatory agent. Different immune diseases can require use of specific auxiliary compounds useful for treating immune diseases, which can be determined on a patient-to-patient basis. For example, the pharmaceutical composition may be administered in combination with one or more suitable adjuvants, e.g., cytokines (IL-10 and IL-13, for example) or other immune stimulators, e.g., chemokines, tumor-associated antigens, and peptides. Suitable adjuvants are known in the art.

Any suitable method or route can be used to administer the antibody polypeptide or the pharmaceutical composition. Routes of administration include, for example, oral, intravenous, intraperitoneal, subcutaneous, or intramuscular administration. For example, the antibody polypeptide can be formulated in a pharmaceutical composition for intravenous administration, which can include a pharmaceutically acceptable carrier. For example, the pharmaceutical composition can comprise 10 mM sodium phosphate, pH 6.5, 25 mM arginine HCl, and 250 mM sucrose. A therapeutically effective dose is included in the formulation.

A therapeutically effective dose of administered antibody polypeptide(s) depends on numerous factors, including, for example, the type and severity of the immune disease being treated, the use of combination therapy, the route of administration of the antibody polypeptide(s) or pharmaceutical composition, and the weight of the patient. A non-limiting range for a therapeutically effective amount of a domain antibody is 0.1-20 mg/kg, and in an aspect, 1-10 mg/kg, relative to the body weight of the patient. The dose of antibody polypeptide(s) can be further guided by the amount of antibody polypeptide(s) required for CD40 antagonism in in vitro and/or in vivo models of disease states.

In certain embodiments, the antibody polypeptide can be administered at a dose of about 75 to about 1500 mg. The dose can be administered once every 2 weeks. Optionally, the dose can be at least 75 mg, at least 225 mg, at least 675 mg, about 75 mg, about 225 mg, about 675 mg, or about 1500 mg. For example, 100 to 750 mg of antibody polypeptide can be administered intravenously. Alternatively, the dose may range from about 200 mg to about 1200 mg, or from about 500 mg to about 1000 mg. The method comprises at least one administration cycle (e.g., 2 weeks). Optionally, at least 2 doses can be administered. In certain embodiments, at least 7 doses are administered. When multiple doses are administered, the doses may be the same or different. For example, the dose can be administered over a set treatment regimen, such as once every two weeks (e.g., on Day 1/Week 0, Week 2, Week 4, Week 6, Week 8, Week 10 and Week 12) for a total of 7 doses.

The following examples are merely illustrative and should not be construed as limiting the scope of this disclosure in any way as many variations and equivalents will become apparent to those skilled in the art upon reading the present disclosure.

The contents of all references, GENBANK® entries, patents and published patent applications cited throughout this application are expressly incorporated herein by reference.

Example 1

Clinical Pharmacology and Safety

The safety and efficacy of BMS-986004 was tested in humans in a double-blind, randomized, placebo-controlled, ascending single dose study in healthy and KLH-challenged male and female (women of non-child bearing potential) subjects (first-in-human study). Placebo or BMS-986004 was administered to 75 healthy subjects at doses of 0.6 mg (Minimal Anticipated Biological Effect Level [MABEL]), 1.3 mg, 3.75 mg, 18.75 mg, 75 mg and 225 mg, representing dose panels 1-6, respectively. Nine subjects in each of dose panel 1-3 were randomized in 2:1 ratio to receive BMS-986004 (N=6) or placebo (N=3). Sixteen subjects in each dose panel 4-6 were randomized in 3:1 ratio to receive BMS-986004 (N=12) or placebo (N=4). Subjects in dose panels 1-4 completed the study and subjects in dose panels 5-6 are completing the study.

No serious adverse events were reported. Non-serious adverse events were reported in 43 of the 75 subjects (57.3%). One hundred and twenty three (123) total adverse events were reported. Of the 123 events, 9 (7.3% of events) were designated as related to the treatment and 114 (92.7% of events) were designated as not related. A total of 7 subjects experienced the related events and include 1 subject in dose panel 3 (1 gingival ulceration), 3 subjects in dose panel 4 (1 aphthous stomatitis, 1 visual field defect, 3 headache [same subject]), 2 subjects in dose panel 5 (1 myalgia, 1 headache) and 1 subject in dose panel 6 (1 dyspnoea). The most commonly reported events were headache (18.7% of subjects), rhinorrhoea (9.3% of subjects), pharyngitis (8.0% of subjects), and cough, upper respiratory tract infection (both 6.7% of subjects), with the majority of events not being related to the treatment.

The System Organ Class (SOC) of Nervous System Disorders accounts for the most commonly reported adverse events with the highest frequency (22.7% of subjects). The most commonly reported adverse event was headache (18.7% of subjects). All events in this SOC were not related with the exception of 5 events (4 headaches and 1 visual field defect) which were related. The SOCs of Respiratory, Thoracic and Mediastinal Disorders, Musculoskeletal and Connective Tissue Disorders, Infections and Infestations and Gastrointestinal Disorders comprise subject's frequencies of 21.3%, 18.7%, 14.7% and 13.3%, respectively. The only infections reported were pharyngitis (8% of subjects) and upper respiratory tract infection (6.7% of subjects), all of which were designated as not related and either Grade 1 or 2. There have been no reports of opportunistic infections, malignancies and thromboembolism (TE) events.

Analyses of dose panel 5 (75 mg) and dose panel 6 (225 mg) indicated that the adverse event profile was comparable in frequency of events and in distribution across SOCs to the adverse event profile for all dose panels combined. The overall frequency of adverse events was 50.0% and 43.8%, in dose panel 5 and dose panel 6, respectively, as compared to 57.3% for all dose panels combined.

Clinical trials investigators observed subjects for any clinical manifestations of both venous and arterial TE. The risk of thromboembolism was further assessed by monitoring changes in TE biomarkers. No significant abnormal changes in a set of primary TE biomarkers (i.e., D-dimer, TAT, prothrombin F1+2, aPTT, troponin I, and platelet count) were identified. In addition, there was no evidence of drug-induced platelet-leukocyte aggregation in vivo or drug-induced increased platelet-leukocyte aggregability in vitro (plateletmonocyte and platelet-neutrophil aggregates were measured at multiple time points by flow cytometry as a sensitive marker of platelet activation).

Hepatic function was carefully assessed in all subjects including alanine aminotransferase [ALT], aspartate aminotransferase [AST] and total bilirubin. There were no clinically significant changes in any of the liver function tests and no indication of drug induced liver injury (per eDISH and Hy's Law assessment). Routine ECGs were performed on all subjects and no subjects have experienced new onset of QTcF values >500 msec following dosing. Furthermore, subjects were closely monitored for red blood cell (RBC) count, hemoglobin concentration, hematocrit and percentage of reticulocytes and there were no observations of anemia. Investigators also monitored subjects for white blood cell parameters which did not reveal any remarkable decreases in laboratory values including absolute neutrophil, absolute lymphocyte and CD4 lymphocyte counts. Serum immunoglobulin levels were also monitored and IgG levels remained above 500 mg/dL with the exception of 3 subjects (1 subject dose panel 4, 2 subjects dose panel 5) who only had transient decreases in IgG below 500 mg/dL. No subjects were removed from the study due to safety issues. Moreover, no safety concerns/criteria to stop dose escalation were met.

Example 2

Pharmacokinetics of BMS-986004

The half-life of the BMS-986004 is stable at doses higher than 18.75 mg, with the half-life approaching approximately 4-5 days at these doses. Maximal serum concentrations occur at the end of infusion, with a multi-exponential decline in concentrations thereafter. Mean exposures ($C_{max}$ and AUC) increase in an approximately dose proportional manner from 18.75 mg.

No clinically significant health risks were identified in the initial in-humans (first-in-humans) study and the safety margins in non-clinical studies were favorable. Thus, BMS-986004 is being evaluated in the ITP patient population.

Example 3

Overall Risk/Benefit Assessment of BMS-986004 in ITP Patients

Administration of BMS-986004 pharmaceutical compositions can normalize platelet counts in the patients with immune thrombocytopenic purpura. The patient's baseline peripheral blood platelet count may at least double after treatment. The patient's peripheral blood baseline platelet count may be greater than or equal to 50,000/mm$^3$ or greater than or equal to 100,000/mm$^3$ after treatment. The patient may demonstrate a peripheral blood platelet count increase of 20,000/mm$^3$ after treatment.

A Phase 1b/2, multicenter, open-label study to evaluate the safety, efficacy, dose response, and pharmacology (PK, target engagement and PD) of BMS-986004 in subjects with ITP is conducted. This study is initiated using a 75 mg, a dose that has demonstrated relatively low immunosuppressive effect and has demonstrated no clinically significant risks in the initial in-human study. Human ITP patients are enrolled sequentially in dose panels in an ascending manner (starting with 75 mg as the lowest dose) upon careful review of all cumulative safety information. Cumulative safety data includes all data that is available in the initial in-human study as well as additional data collected during the ITP study.

ITP subjects derive clinical benefit from BMS-986004 and help guide dose selection and design of future studies in the clinical development of BMS-986004. Primary efficacy assessments include the proportion of patients achieving a platelet count of at least ≥30,000/mm$^3$, at least a 2-fold increase in their platelet count from the baseline count, and absence of bleeding. (According to the International Working Group on ITP, the "absence of bleeding" can include minor bleeding symptoms, such as single instance of grade 1 bleeding symptoms in the skin, which may be unrelated to ITP. See Rodeghiero et al., *Blood*, 113(11):2386-2393 (2009).)

Example 4

Patient Inclusion and Exclusion Criteria

BMS-986004 can be used in subjects suffering from persistent or chronic ITP, as defined by American Society of Hematology (ASH) guidelines. The human subjects can have a peripheral blood platelet count of less than 30,000/mm$^3$ before treatment. The human patient can have a peripheral blood platelet count of less than 100×10$^9$ L or 50×10$^9$ L before treatment. These subjects may have failed conventional therapies including immunosuppressive therapies, splenectomy and TPO mimetics/agonists. Previous treatments for ITP can, for example, include corticosteroids, immunoglobulins, azathioprine, danazol, cyclophosphamide and/or rituximab. The human patient may have been splenectomized prior to treatment. Subjects can be refractory or relapsed after at least one prior ITP therapy, i.e., failed to achieve a sustained (for more than 3 month) platelet count ≥50,000/mm$^3$ to other prior ITP therapies.

Patients for the study in Example 15 are selected based on the following criteria: Screening evaluations to determine subject eligibility are performed 21 days prior to study drug administration. A patient's platelet count (calculated from the mean of 2 counts taken within a week, during the screening and pre-treatment periods) is less than 35,000/mm$^3$. The patient's platelet count is stable and/or declining and may not present with an upward trend, based on the mean of two determinations taken within a week.

The screened patient's complete blood count is within the reference range (including white blood count [WBC] differential not indicative of a disorder other than ITP), with the following exceptions:
  subjects with hemoglobin levels between 9 g/dL for females and 10 g/dL for males and the lower limit of normal (LLN) are eligible for inclusion, if anemia was clearly attributable to ITP (excessive blood loss);
  absolute neutrophil count (ANC) greater than or equal to 1500/μL (elevated WBC/ANC due to corticosteroid treatment is acceptable);
Prothrombin Time/International Normalized Ratio (PT/INR) and activated partial thromboplastin time (aPTT) is within 80% to 120% of the normal range with no known hypercoagulable state. The patient's following clinical chemistries are monitored so they do not exceed 2 times the normal reference range: ALT, AST, alkaline phosphatase, and bilirubin >1.5 times upper limit normal (ULN) (isolated bilirubin >1.5×ULN is acceptable if bilirubin is fractionated and direct bilirubin is <35%). The patient's Albumin for deviations outside of 80 to 120% of normal range.

Female patients of childbearing potential must have a negative serum or urine pregnancy test (minimum sensitivity 25 IU/L or equivalent units of HCG) within 24 hours prior to the start of study drug administration. Female patients cannot be breastfeeding. Female patients of childbearing potential must use contraception for the duration of treatment with study drug (84 days) plus 5 half-lives of study drug (20 days) plus 30 days (duration of ovulatory cycle) for a total of 134 days post-treatment completion. Males who are sexually active with female patients of childbearing potential must use contraception for the duration of treatment with study drug (84 days) plus 5 half-lives of the study drug (20 days) plus 90 days (duration of sperm turnover) for a total of 194 days post-treatment completion. Azoospermic males and WOCBP who are continuously not heterosexually active are exempt from contraceptive requirements. However they must still undergo pregnancy testing.

Enrolled patients do not have secondary immune thrombocytopenia, e.g., due to SLE, CLL, CVID, APS or drug induced thrombocytopenia. Enrolled patients also do not have a History of MDS (Myelodysplastic Syndrome). Enrolled patients do not exhibit an identifiable alternative cause of their thrombocytopenia, such as splenomegaly, family thrombocytopenia, bacteraemia, sepsis or active infection requiring or not therapy. In addition, enrolled patients do not have:
  any severe medical condition (cardiac, hepatic or renal disorder) other than chronic ITP. (Note: "Severe" is defined as Grade 3 and above as a rule according to guidelines described by the Common Terminology Criteria for Adverse Events, Version 4.03);
  a history of thromboembolic disease within the last 24 month (e.g., transient ischemic attack [TIA], stroke [CVA], pulmonary embolism [PE]), history of deep vein thrombosis (DVT) or thrombotic complications);
  a history of significant cardiovascular disease (e.g., congestive heart failure [CHF] New York Heart Association Grade III/IV, arrhythmia known to increase the risk of thromboembolic events [e.g., atrial fibrillation], subjects with a QT interval corrected for heart rate of >450 msec, angina, coronary artery stent placement, angioplasty, coronary artery bypass grafting);
  an inability to be venipunctured and/or tolerate venous access; or
Patients can also be excluded for the following physical and laboratory test findings:
  clinically significant abnormalities in coagulation biomarkers;
  an abnormal (positive) direct Coombs' test in patients who have not received IVIg within 30 days;
  a positive blood screen for Hepatitis C antibody;
  a positive blood screen for HIV-1, -2 antibodies or p24 antigen (HIV viral RNA test may be conducted if the investigator deems necessary);
  a positive test for active Hepatitis B infection as indicated by screening using Hepatitis B surface antigen (HBsAg), Hepatitis B surface antibody (anti-HBs) and Hepatitis B core antibody (anti-HBc) (See Appendix 3);
  a positive QuantiFERON TB test;
  evidence of organ dysfunction or any clinically significant deviation from normal in physical examination, vital signs, ECG or clinical laboratory determinations beyond what is consistent with the target population.

Patients with a history of serious adverse reaction or hypersensitivity to IV administered biological therapeutic, or a history of any significant drug allergy (such as anaphylaxis or hepatotoxicity) are also excluded from the study. Prisoners who are involuntarily incarcerated or compulsorily detained for treatment of either a psychiatric or physical (e.g., infectious disease) illness are not included in the study. Finally, patients with prior exposure to BMS-986004 are not included.

Enrolled patients also have indicated they have not used the following medications or been subject to the following treatments within the time periods indicated below:
  Within 180 days prior to first dose:
    Intravenous (IV) cyclophosphamide;
    3 or more courses of systemic corticosteroids administered for concomitant conditions;
    Rituximab;
  Within 90 days prior to first dose:
    High dose dexamethasone (40 mg/day IV) for treatment of ITP;

Within 60 days prior to first dose:
  A non-biologic investigational agent;
  Any other immunosuppressive/immunomodulatory agent (including mycophenylate mofetil, cyclophosphamide, sirolimus) with the exception of danazol, azathioprine, and corticosteroids;
Within 30 days before first dose:
  Splenectomy;
  Blood transfusion;
  Intravenous immunoglobulin;
  Corticosteroids greater than 10 mg/day (prednisone or prednisone equivalent).

Example 5

Phase 1b/2 Study Design

The study is divided into three phases: a Response Phase (6 weeks), a Remission Phase (6 weeks) and a Follow Up Phase (4 weeks). Following screening, a total of 40 evaluable subjects are enrolled in the study. Subjects are considered evaluable if they receive the first 4 doses of study drug and complete the required safety and efficacy evaluations at Day 50. Non-evaluable subjects are replaced to maintain a count of 10 subjects in each dose panels.

Subjects are treated in dose panels of 10 subjects each. Four (4) dose panels are enrolled sequentially in an ascending manner (about 75 mg to about 1500 mg), with dose intensity selected to provide increased levels of immunosuppression at steady state.

BMS-986004 is administered once every 2 weeks as an IV infusion for a total of 7 doses. Four (4) doses are administered during the Response Phase over a 6 week treatment period. The remaining 3 doses are administered during the Remission Phase of the study over a 6 week treatment period. Subjects receive investigational product on Day 1/Week 0, Week 2, Week 4, Week 6, Week 8, Week 10 and Week 12, for a total of 7 doses.

Each dose cohort will include 10 new subjects, and will receipt the respective dose level at Day1/Week 0, regardless of the number of subjects joining a dose cohort because of intra-subject dose escalation. A new cohort is opened to treat subjects at a dose lower than 75 mg if at least 6 subjects treated at the 75 mg cohort achieve platelet Response (R) (platelet count ≥30,000/mm³ and at least 2-fold increase from the baseline count and absence of bleeding), at the end of response phase (Week 6). The new cohort follows the same schedule as the other cohorts including intra-subject dose escalation.

Example 6

Preparation of and Intravenous Administration of BMS-986004

BMS-986004 is a clear to slightly opalescent, colorless to pale yellow solution that may contain particulate matter upon visual inspection. The drug product is a preservative free, ready to use solution contained in a 10 cc vial with 20 mm opening, Type I flint glass, 1-panel, open label. Each vial of drug product contains the labeled amount of BMS-986004, 190 mg/vial (50 mg/mL) in 10 mM sodium phosphate, pH 6.5, 25 mM arginine HC1, 250 mM sucrose. A 13% overfill is included in each vial to account for vial, needle syringe (VNS) holdup. This drug formulation is used for intravenous administration only.

Dilution of BMS-986004 Injection for IV use is performed using sterile disposable syringes. Prior to IV administration, BMS-986004 Injection is diluted with 0.9% Sodium Chloride Injection (NS) to prepare dosing solutions with BMS-986004 concentrations ranging from 1.5 to 30 mg/mL. Table 1 below indicates the total dose and number of vials per dose for each treatment.

TABLE 1

Dosing Summary

| Treatment | Total Daily Dose | Volume of Reconstituted 50 mg/mL BMS-986004 | Number of BMS-986004 Vials | Prime Filter | Infusion Volume (mL) | Infusion Time (min) | Rate (mg/min) |
|---|---|---|---|---|---|---|---|
| 1 | 75 mg IV | 3 mL | 1 | YES | 50 | 120 | 0.625 |
| 2 | 225 mg IV | 4.5 mL | 2 | NO | 100 | 120 | 1.875 |
| 3 | 675 mg IV | 13.5 mL | 4 | NO | 100 | 120 | 5.625 |
| 4 | 1500 mg IV | 30 mL | 8 | NO | 100 | 120 | 12.500 |

The study drug is administered as an infusion using an infusion pump. The product is infused over at most 2 hours for each patient, using a volumetric pump at the protocol specific dose(s) and rate(s) through the IV infusion.

Vital signs (blood pressure, heart rate, respiratory rate, and temperature) are monitored before infusion (at anytime the day of dosing, prior to infusion), approximately every 15 minutes during infusion, at the end of the infusion (within 10 minutes after the infusion has stopped), and approximately every 30 minutes after completion of the infusion until stable, as judged by the investigator. When an anaphylactoid-like infusion reaction or anaphylactic reaction occurs, vital signs are taken more frequently, as warranted by the severity of the reaction. Blood pressure and heart rate are also taken prior to discharge from the site on visits in which study drug is administered.

Physical examinations, vital sign measurements, 12-lead electrocardiograms (ECG), and clinical laboratory evaluations are performed at selected times throughout the dosing interval. Subjects are closely monitored for adverse events throughout the study. Blood samples are collected for up to 336 hours after study drug administration for pharmacokinetic (PK) analysis. Approximately 553 mL of blood is drawn from each subject during the study. The approximate duration of the study is 20 weeks (approximately 140 Days). This includes a 21 day screening period, a 12 week treatment period, and a 1 month follow up period. The end of study is defined as the date of the last visit of the last subject undergoing the study.

Example 7

Biomarker Assessments

Blood is drawn for the measurement of the following antibody target engagement, PD and disease-related biomarkers.

The treatment may produce at least one therapeutic effect measurable by a biomarker selected from the group consisting of platelet response/complete response (R/CR), platelet count, CD40L receptor occupancy, platelet associated anti-platelet antibodies, platelet Ag-specific B cells, platelet antigen-specific B cells, plasma soluble free CD40L level, plasma soluble total CD40L level, plasma cell-associated whole blood gene expression in peripheral blood, B cell repertoire analysis, and immune cell counts (T, B, and NK). The treatment may not produce adverse effects measurable by a biomarker selected from the group consisting of platelet-leukocyte aggregation, plasma d-Dimer, plasma Thrombin anti-Thrombin (TAT), serum troponin 1, activated partial thromboplastin time (aPTT), and electrocardiography (ECG), C-relative protein (CRP), immunoglobulin (IgM, IgG, IgA), immune cell counts (T, B, and NK) and phenotypes.

Primary Safety (TE) Biomarker Assessments

Previous molecules in clinical development targeting CD40L have demonstrated the potential to induce thromboembolism (TE). All data from nonclinical, non-human primate and single ascending dose clinical study of BMS-986004 are consistent with the conclusion that BMS-986004 does not possess platelet activating or other activity associated with the induction of TE. To further mitigate the risk of TE in subjects dosed with BMS-986004, a set of primary, accepted markers of platelet activation and TE potential are monitored at frequent intervals and analyzed in real-time. Plasma and serum are collected to monitor the risk and minimize impact of a potential TE event. Prothrombin time (PT) and activated Partial thromboplastin time (aPTT) are assessed at screening to exclude patients with evidence of a hypercoagulable state. D-dimer and thrombin anti-thrombin (TAT) in plasma are quantified as measures of TE risk. Serum troponin I is monitored as an indicator of potentially TE-related subclinical myocardial infarction. Data from these primary safety biomarker measurements are be collected and carefully evaluated in the context of a thorough review of all available clinical data and used to formulate go/no-go decisions prior to dose escalation.

Target Engagement Biomarker Assessment

Target engagement (TE) in vivo is evaluated at frequent intervals post-dosing using a CD40L receptor occupancy (RO) assay. Binding of BMS-986004 to CD40L on CD4+ T cells in whole blood is determined by flow cytometry-based measurements of the decrease in signal from a competitive, fluorescently-labeled, CD40L-specific antibody relative to the pre-dose signal.

Exploratory Biomarker Assessments

In addition to confirming target engagement by RO, exploratory PD biomarkers are measured to provide evidence of disease-relevant and pathway-specific in vivo biological activity. Platelet associated anti-platelet antibody titers are measured by immunoassay and platelet Ag-specific B cells are enumerated by ELISPOT to assess the effects of BMS-986004 on anti-platelet autoimmune activity. B cell repertoire is interrogated by high throughput sequencing of B cell receptor genes. Free and total soluble CD40L is measured by immunoassay and LC/MS, respectively, as measures of target engagement and target load. Peripheral blood expression of genes previously shown to be modulated by the presence of BMS-986004 in pre-clinical and the single-ascending dose clinical studies as well as genes associated with cell types of interest, such as plasma cells, are measured by microarray and/or RT-PCR based technologies.

Exploratory Safety Biomarker Assessments

Serum and cell-based biomarkers are assessed to evaluate the effect of BMS-986004 on protective immunity. Serum immunoglobulin (IgG, IgM, IgA) levels are measured to monitor humoral immunity. The presence of protective immunity against viral re-activation is assessed by measuring viral serology (anti-EBV, anti-CMV, anti-HBV). Surveillance for acute inflammation is supported by regular measurement of serum CRP. Finally, any effects of repeat dosing of BMS-986004 on immune cell subsets is evaluated by regular cell enumeration (T, B and NK cell counts) and cell phenotyping by whole blood flow cytometry.

Example 8

Intra-Subject Dose Escalation

Intra-subject dose escalation occurs after the subject has completed the Response Phase of the study, if at all. The intra-subject dose escalation decision is based on review of the safety information and platelet count after 4 weeks of treatment. The decision to escalate the dose for a subject is made after evaluating platelet count at Day 50, 7 days after the 4th dose of BMS-986004 is administered. A subject receives the next higher dose of BMS-986004 if a clinically significant response has not been achieved based on measurement of platelet count on the last two consecutive counts performed at Day 43 and Day 50, and a favorable safety profile is observed. A clinically significant response is defined as achieving a platelet count $\geq 50,000/mm^3$, with an increase of at least $20,000/mm^3$ from the subject's baseline platelet count prior to treatment and absence of bleeding. The subject is then dosed at the higher dose level for the remainder of the study (Remission Phase), receiving investigational product at that dose on Week 8, Week 10, and Week 12. The active treatment period with BMS-986004, regardless of the dose, may not exceed 12 weeks for any individual subject.

If a subject's platelet count exceeds $450,000/mm^3$ as indicated by the two consecutive platelet count measurements, dosing of BMS-986004 is stopped. Otherwise, the subject remains in the study, and platelet counts are assessed based on the normal study visit schedule. Dosing of BMS-986004 is reinitiated only after discussion between Study Director and Investigator if clinically appropriate and dictated by the medical judgment and subject's safety.

Decisions regarding dose escalation are made based on the review of all cumulative safety information which includes the safety data through study Day 15 from the first 5 subjects in the preceding lower dose cohort. Escalation to the next higher cohort occurs when 5 subjects in a cohort have been followed for at least 2 weeks and none of the stopping rules have been met, if at all. If none of the stopping rules is present in dose panel, then dose escalation proceeds within the next higher dose level.

The selected dose for a cohort does not exceed the originally planned dose for that cohort, i.e., selected dose for cohort C should not be larger than 675 mg and it should be at most 1500 mg for cohort D.

The stopping rules listed below are used to determine whether it is safe to escalate an enrolled patient in to the next higher cohort. Dose escalation to the next planned dose does not proceed if any of the following criteria are met (Adverse event grading as defined by the Common Terminology Criteria for Adverse Events [CTCAE, Version 4.0]):

Four or more subjects in a cohort have platelet counts >450,000/mm$^3$,

Two or more subjects have serious adverse events in the same organ system (Grade 3 and above), that are determined to be related to study medication, It is determined that the limit of safety and/or tolerability has been reached, as determined by the Study Team and the Investigator.

Other reasons to halt dose escalation include, but are not limited to, observing a single serious adverse event in individual subjects, observing trends in a given dose panel and across dose panels, and determining that the limit of safety and/or tolerability has been reached, as determined by the Study Team and the Investigator.

Figure 2:
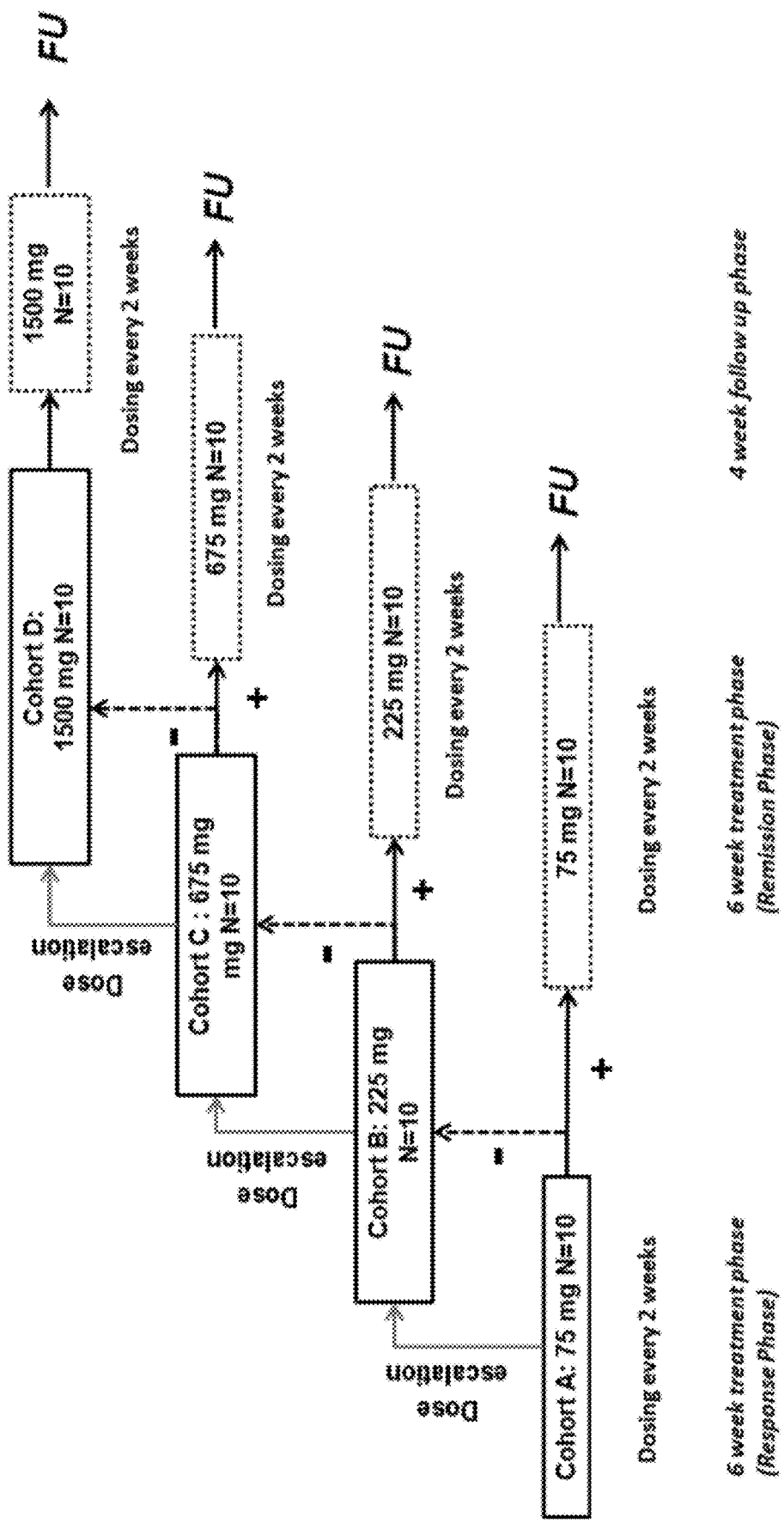
FIG. 2 shows an FDA Phase 1b/2 study dose escalation schematic.
Figure 3:
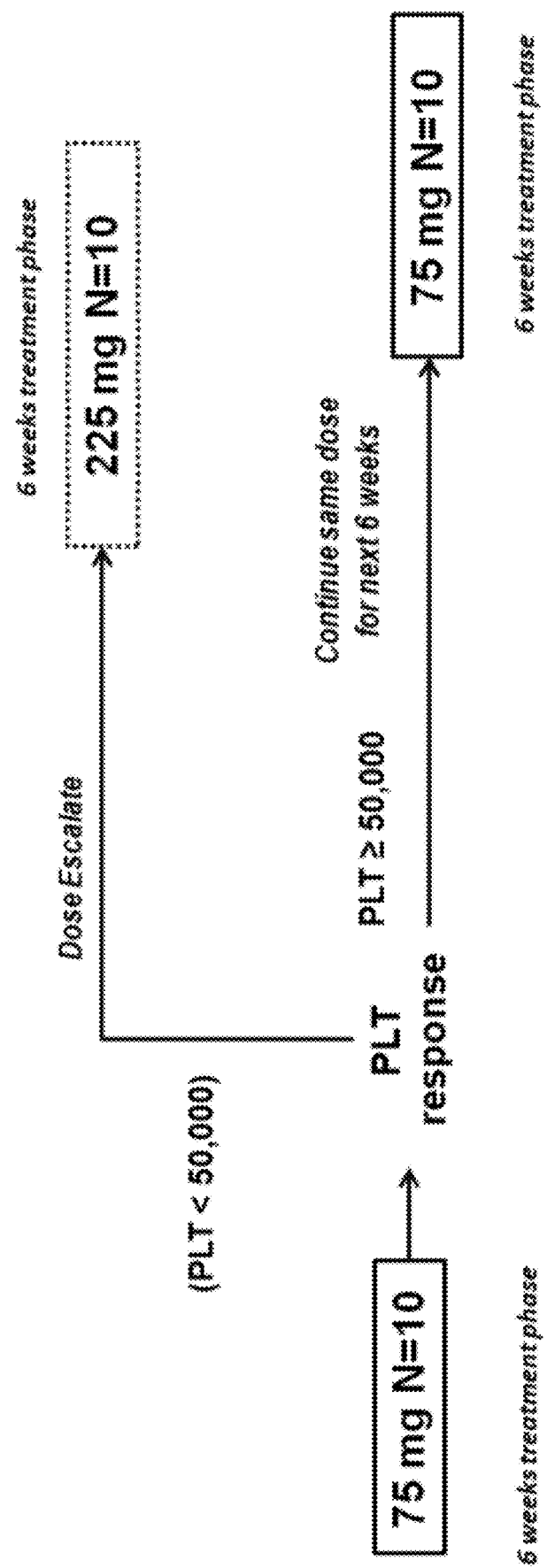
FIG. 3 shows an FDA Phase 1b/2 study schematic for intra-subject dose escalation.

If any of the above criteria are met within a dose level, the progression to a higher dose level is put on hold and all safety data available across the study is evaluated to estimate the risk of proceeding to the higher dose level. The review will include all of the subject(s) that experienced SAEs listed above. In addition, the data set may include subjects from a dose panel, the entire dose panel, or if appropriate, all randomized subjects treated to date. If dose escalation is stopped due to any of these findings, additional cohorts may receive the same or lower doses of the investigational compound. At the time of dose escalation, dose levels of new cohorts are adjusted to lower doses if the accumulated safety data so dictates. The study design schematic is presented in FIGS. 2 and 3.

Although the present embodiments have been described in detail with reference to examples above, it is understood that various modifications can be made without departing from the spirit of these embodiments, and would be readily known to the skilled artisan.

What is claimed is:

1. A method of treating an immune disease in a patient, comprising administering to the patient a therapeutically effective amount of an antibody polypeptide which comprises: (1) a variable domain comprising the amino acid sequence of SEQ ID NO: 5; and (2) a human Fc domain, wherein at least one dose of the antibody polypeptide is administered every two weeks at a dose of about 75 mg to about 1500 mg.

2. The method of claim 1, wherein the variable domain of the antibody polypeptide comprises: (1) a CDR1 region having the amino acid sequence of SEQ ID NO: 2; (2) a CDR2 region having the amino acid sequence of SEQ ID NO: 3; and (1) a CDR3 region having the amino acid sequence of SEQ ID NO: 4.

3. The method of claim 1, wherein the antibody polypeptide comprises the amino acid sequence of SEQ ID NO: 6.

4. The method of claim 1, wherein the immune disease is primary immune thrombocytopenia (ITP).

5. The method of claim 1, wherein the dose is selected from about 75 mg, about 225 mg, about 675 mg, and about 1500 mg.

6. The method of claim 1, wherein the dose is from about 200 mg to about 1200 mg.

7. The method of claim 1, wherein the antibody polypeptide is formulated in a pharmaceutical composition for intravenous administration.

8. The method of claim 7, wherein the pharmaceutical composition comprises a pharmaceutically acceptable carrier.

9. The method of claim 1, wherein the antibody polypeptide is administered intravenously.

10. The method of claim 1, wherein at least 2 doses are administered, and the at least 2 doses are the same.

11. The method claim 1, wherein at least 7 doses are administered.

12. The method of claim 1, wherein the therapeutically effective amount of the antibody polypeptide normalizes platelet counts in the patient.

13. The method of claim 1, wherein the patient has a peripheral blood platelet count that increases by at least $20,000/mm^3$ after treatment.

14. The method of claim 1, wherein the patient has a peripheral blood platelet count of less than $30,000/mm^3$ before treatment.

15. The method of claim 1, wherein the patient was splenectomized prior to treatment.

16. The method of claim 1, wherein the method further comprises administering an immunosuppressive/immunomodulatory and/or anti-inflammatory agent to the human patient.

* * * * *

UNITED STATES PATENT AND TRADEMARK OFFICE
CERTIFICATE OF CORRECTION

PATENT NO. : 11,466,091 B2
APPLICATION NO. : 16/795823
DATED : October 11, 2022
INVENTOR(S) : Marek Honczarenko et al.

Page 1 of 1

It is certified that error appears in the above-identified patent and that said Letters Patent is hereby corrected as shown below:

In the Claims

At Column 30, Line 16, Claim 11, after "method" Insert -- of --

Signed and Sealed this
Twentieth Day of June, 2023

Katherine Kelly Vidal
*Director of the United States Patent and Trademark Office*

SEQUENCE LISTING

```
<160> NUMBER OF SEQ ID NOS: 6

<210> SEQ ID NO 1
<211> LENGTH: 261
<212> TYPE: PRT
<213> ORGANISM: Homo Sapien

<400> SEQUENCE: 1

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240
```

```
Val Thr Asp Pro Ser Gln Val Ser His Gly Thr Gly Phe Thr Ser Phe
                245                 250                 255

Gly Leu Leu Lys Leu
            260

<210> SEQ ID NO 2
<211> LENGTH: 5
<212> TYPE: PRT
<213> ORGANISM: Artificial
<220> FEATURE:
<223> OTHER INFORMATION: CDR1 Region

<400> SEQUENCE: 2

Trp Glu Leu Met Gly
1               5

<210> SEQ ID NO 3
<211> LENGTH: 17
<212> TYPE: PRT
<213> ORGANISM: Artificial
<220> FEATURE:
<223> OTHER INFORMATION: CDR2 Region

<400> SEQUENCE: 3

Gly Ile Glu Gly Pro Gly Asp Val Thr Tyr Tyr Ala Asp Ser Val Lys
1               5                   10                  15

Gly

<210> SEQ ID NO 4
<211> LENGTH: 7
<212> TYPE: PRT
<213> ORGANISM: Artificial
<220> FEATURE:
<223> OTHER INFORMATION: CDR3 REGION

<400> SEQUENCE: 4

Lys Asp Ala Lys Ser Asp Tyr
1               5

<210> SEQ ID NO 5
<211> LENGTH: 118
<212> TYPE: PRT
<213> ORGANISM: Artificial
<220> FEATURE:
<223> OTHER INFORMATION: Variable Region

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Trp Glu
            20                  25                  30

Leu Met Gly Trp Ala Arg Gln Ala Pro Gly Lys Gly Leu Glu Trp Val
        35                  40                  45

Ser Gly Ile Glu Gly Pro Gly Asp Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Val Gly Lys Asp Ala Lys Ser Asp Tyr Arg Gly Gln Gly Thr
            100                 105                 110

Leu Val Thr Val Ser Ser
```

115

<210> SEQ ID NO 6
<211> LENGTH: 353
<212> TYPE: PRT
<213> ORGANISM: Artificial
<220> FEATURE:
<223> OTHER INFORMATION: Fusion Protein

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Trp Glu
            20                  25                  30

Leu Met Gly Trp Ala Arg Gln Ala Pro Gly Lys Gly Leu Glu Trp Val
        35                  40                  45

Ser Gly Ile Glu Gly Pro Gly Asp Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Val Gly Lys Asp Ala Lys Ser Asp Tyr Arg Gly Gln Gly Thr
            100                 105                 110

Leu Val Thr Val Ser Ser Ala Ser Thr Glu Pro Lys Ser Ser Asp Lys
        115                 120                 125

Thr His Thr Ser Pro Pro Ser Pro Ala Pro Glu Leu Leu Gly Gly Ser
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Asp Glu Leu Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

```
Ala Leu His Asn His Tyr Thr Gln Lys Ser Leu Ser Leu Ser Pro Gly
            340                 345                 350
Lys
```